(12) United States Patent
Lalla

(10) Patent No.: US 8,525,560 B2
(45) Date of Patent: Sep. 3, 2013

(54) DRIVER CIRCUIT FOR A MEASURING TRANSDUCER AS WELL AS MEASURING SYSTEM FORMED THEREWITH

(75) Inventor: Robert Lalla, Lorrach (DE)

(73) Assignee: Endress + Hauser Flowtec AG, Reinach (CH)

( * ) Notice: Subject to any disclaimer, the term of this patent is extended or adjusted under 35 U.S.C. 154(b) by 204 days.

(21) Appl. No.: 13/089,444

(22) Filed: Apr. 19, 2011

(65) Prior Publication Data

US 2011/0271756 A1 Nov. 10, 2011

(30) Foreign Application Priority Data

Apr. 19, 2010 (DE) .................. 10 2010 015 586

(51) Int. Cl.
 *H03B 1/00* (2006.01)
(52) U.S. Cl.
 USPC .......................................... 327/112
(58) Field of Classification Search
 USPC .......................... 327/374–377, 112
 See application file for complete search history.

(56) References Cited

U.S. PATENT DOCUMENTS

| 7,394,298 | B2 * | 7/2008 | Hazucha et al. | 327/108 |
| 7,808,286 | B1 * | 10/2010 | Miller et al. | 327/112 |
| 8,018,255 | B2 * | 9/2011 | Hirao et al. | 327/108 |
| 2009/0021228 | A1 | 1/2009 | Carr | |

FOREIGN PATENT DOCUMENTS

| GB | 2 306 064 A | 4/1997 |
| WO | WO 2006/072541 A2 | 7/2006 |

OTHER PUBLICATIONS

English translation of the IPR, Nov. 1, 2012, WIPO, Geneva.
International Search Report dated Jul. 6, 2011, EPO The Netherlands.

\* cited by examiner

*Primary Examiner* — Hai L Nguyen
(74) *Attorney, Agent, or Firm* — Bacon & Thomas, PLLC

(57) ABSTRACT

A driver circuit having: a voltage controller ($UC_D$), which delivers a direct voltage ($U_{PD}$) to a controller output; a direct voltage converter (DC/DC), to which is applied on the primary side the direct voltage ($U_{PD}$) delivered from the voltage controller, and which converts such into a direct voltage ($U'_{PD}$) available on the secondary side; and an end stage operated by means of said direct voltage ($U'_{PD}$), which converts a control signal ($\sin_{exc\_A}$) lying on a signal input into a driver signal ($i_{exc}$) for the measuring transducer. The direct voltage ($U'_{PD}$) available on the secondary side of the direct voltage converter (DC/DC) has, in such case, a magnitude which is always smaller than a magnitude of the direct voltage ($U_{PD}$) delivered by the voltage controller, and the driver signal ($i_{exc}$) has an electrical power ($P_{exc}$), which is higher than an electrical power ($P_{sin}$) of the control signal ($\sin_{exc\_A}$).

46 Claims, 3 Drawing Sheets

DRIVER CIRCUIT FOR A MEASURING TRANSDUCER AS WELL AS MEASURING SYSTEM FORMED THEREWITH

TECHNICAL FIELD

The invention relates to a driver circuit for an actuator, as well as to a transmitter electronics, especially an intrinsically safe transmitter electronics, formed therewith, and, respectively, to a measuring system with such a transmitter electronics, especially a measuring system embodied as a two-conductor, field device.

BACKGROUND DISCUSSION

In industrial measuring and automation technology, for producing measured value signals representing measured variables in analog or digital form, measuring systems installed on-site or near to the process—so called field devices—are applied. The particular measured variables to be registered can be, for example, mass flow, e.g. mass flow rate, density, viscosity, fill level or limit level, pressure, temperature, etc. of a flowable—thus, for example, liquid, powdered, vaporous or gaseous—medium, which is conveyed or held in a corresponding process container, such as, for example, a pipeline or a tank. Further examples for such field devices, known to those skilled in the art, are described at length and in detail in, among others, DE-A 39 34 007, EP-A 1 058 093, EP-A 1 158 289, EP-A 525 920, EP-A 984 248, U.S. Pat. No. 3,764,880, U.S. Pat. No. 3,878,725, U.S. Pat. No. 4,308,754, U.S. Pat. No. 4,317,116, U.S. Pat. No. 4,468,971, U.S. Pat. No. 4,524,610, U.S. Pat. No. 4,574,328, U.S. Pat. No. 4,594,584, U.S. Pat. No. 4,617,607, U.S. Pat. No. 4,656,353, U.S. Pat. No. 4,768,384, U.S. Pat. No. 4,850,213, U.S. Pat. No. 4,926,340, U.S. Pat. No. 5,024,104, U.S. Pat. No. 5,052,230, U.S. Pat. No. 5,068,592, U.S. Pat. No. 5,131,279, U.S. Pat. No. 5,207,101, U.S. Pat. No. 5,231,884, U.S. Pat. No. 5,359,881, U.S. Pat. No. 5,363,341, U.S. Pat. No. 5,416,723, U.S. Pat. No. 5,469,748, U.S. Pat. No. 5,535,243, U.S. Pat. No. 5,604,685, U.S. Pat. No. 5,672,975, U.S. Pat. No. 5,687,100, U.S. Pat. No. 5,742,225, U.S. Pat. No. 5,742,225, U.S. Pat. No. 5,796,011, U.S. Pat. No. 5,959,372, U.S. Pat. No. 6,006,609, U.S. Pat. No. 6,014,100, U.S. Pat. No. 6,140,940, U.S. Pat. No. 6,236,322, U.S. Pat. No. 6,269,701, U.S. Pat. No. 6,285,094, U.S. Pat. No. 6,311,136, U.S. Pat. No. 6,397,683, U.S. Pat. No. 6,476,522, U.S. Pat. No. 6,480,131, U.S. Pat. No. 6,487,507, U.S. Pat. No. 6,512,358, U.S. Pat. No. 6,535,161, U.S. Pat. No. 6,574,515, U.S. Pat. No. 6,577,989, U.S. Pat. No. 6,662,120, U.S. Pat. No. 6,769,301, U.S. Pat. No. 6,776,053, U.S. Pat. No. 6,799,476, U.S. Pat. No. 7,200,503, U.S. Pat. No. 7,630,844, US-A 2008/0015799, WO-A 00/14 485, WO-A 00/26739, WO-A 00/36 379, WO-A 00/48157, WO-A 00/67087, WO-A 01/02816, WO-A 02/086426, WO-A 02/103327, WO-A 02/45045, WO-A 2004/048905, WO-A 2005/040735, WO-A 2006/130087, WO-A 2010/014102, WO-A 88/02476, WO-A 88/02853, and WO-A 95/16897. The measuring systems shown therein have, in each case, a physical-to-electrical measuring transducer for registering the particular measured variable(s), as well as, electrically connected therewith, a transmitter electronics, which is most often externally supplied with electrical energy and which has a driver circuit controlling the measuring transducer; as well as having a measuring and operating circuit for producing measured values representing the at least one measured variable.

The measuring transducer is, in each case, provided so as to be inserted into a wall of the container in each case conveying the medium, or into the course of a line, for example, a pipeline, in each case conveying the medium and serves to produce at least one electrical measurement signal representing the at least one measured variable. For such purpose, the particular measuring transducer, and consequently an actuator provided therein, is, during operation of the measuring system, operated by a driver signal—which is, for example, bipolar and/or at least at times periodic—generated by the driver circuit provided in the transmitter electronics, and driven in such a manner, that it acts on the medium in suitably for the measuring, in order to cause reactions there which correspond with the measured variable to be registered, and which are correspondingly convertible into the at least one measurement signal. In such case, the driver signal can, for example, be an analog or also a suitably clocked binary signal correspondingly controlled with regard to an electrical current level, a voltage level and/or a signal frequency. As examples of such active—thus correspondingly converting an electrical driver signal by means of a (for example, predominantly inductive) actuator into a measurable effect useful for registering the measured variable—measuring transducers are to especially be mentioned HF transmitting/receiving transducers working according to the echo principle, or flow-measuring transducers, serving for measuring flowing media, having at least one coil which is driven by the driver signal and producing a magnetic field, and also, for example, measuring transducers of vibration type having at least one vibrating measuring tube, and an electro-mechanical oscillation exciter acting thereon, or at least one ultrasonic transmitter driven by the driver signal, etc. For the purpose of producing measured values representing the measured variable(s) to be registered by means of the measuring system, the at least one measurement signal is, later in the course of the procedure, fed to a measuring and operating circuit, which is provided in the transmitter electronics and, for example, also formed by means of a microcontroller and/or by means of a digital signal processor. For accommodating the transmitter electronics, the field devices additionally include an electronics housing, which, as for example is provided in U.S. Pat. No. 6,397,683 or WO-A 00/36379, is arranged at a distance from the measuring transducer and can be connected with this via only a flexible line, or which, as for example also shown in EP-A 903 651 or EP-A 1 008 836, is arranged directly on the measuring transducer or on a measuring transducer housing separately housing the measuring transducer.

Measuring systems of the described type are additionally, usually via a data transmission system connected to the transmitter electronics, connected with one another and/or with corresponding process control computers, to which they transmit the measured value signals, e.g. via a (4 mA to 20 mA) current loop and/or via a digital data bus, and/or from which they receive operating data and/or control commands in a corresponding manner. Serving in such case as data transmission systems are fieldbus systems—especially serial fieldbus systems—such as, for example PROFIBUS-PA, FOUNDATION FIELDBUS, as well as the corresponding transmission protocols. By means of the process control computers, the transmitted measured value signals can be further processed, and, as corresponding measurement results, be, for example, visualized on monitors, or, for example, also be converted into control signals for actuating devices, such as, for example magnetic valves, electric motors etc., which serve for process control. Measuring systems of the type being discussed are additionally often embodied in such a manner, that they satisfy the requirements for intrinsic explosion safety. In accordance therewith, the field devices are operated with such a low electrical power that, failing to achieve ignition conditions, sparks or arcs cannot be electrically triggered. Intrinsically safe explosion protection is provided, for example, according to the European standards EN 50 014 and EN 50 020 or the ignition protection type "intrinsic safety (Ex-i)" defined therein, is met when electronic apparatuses, and consequently field devices, are embodied in such a manner, that the maximum electrical currents, voltages and powers occurring therein in no case exceed predetermined electrical current, voltage and power limit values. Namely, limit values are, in each case, selected in such a manner, that, in the case of a malfunction—for instance, a short-circuit—the maximum released energy is not sufficient to produce an ignition-capable spark, and, respectively, the maximum converted electrical power does not exceed 1 W (=Watt). The voltage can be held beneath the predetermined limit values for example via Z-diodes, the electrical current for example via resistors, and the power via a corresponding combination of voltage limiting and electrical current-limiting components. Modern measuring systems of the type being discussed are additionally often so-called two-conductor field devices, that is such field devices, in the case of which the transmitter electronics is electrically connected with the external electrical energy supply only via a single pair of electrical lines, thus forming a current conducting loop, and is flowed through by an electrical supply current fed by the energy supply, and in the case of which the transmitter electronics also transmits the instantaneous measured value via the same pair of electrical lines to an evaluation unit provided in the external electrical energy supply and/or electrically coupled with this. The transmitter electronics comprises, in such case, a so-called two-conductor connection circuit having a series current controller flowed through by the electrical supply current for setting and/or modulating—especially clocking—the supply current as a function of the instantaneous measured value, as well as a parallel current controller for setting a stabilized input voltage serving as an internal supply voltage of the transmitter electronics, or for leading away an excess part of the electrical supply current not instantaneously required for producing the measured values.

Examples for such measuring systems embodied as—in given cases, also intrinsically safe—two-conductor field devices can, among other things, be taken from WO-A 05/040735, WO-A 04/048905, WO-A 02/45045, WO-A 02/103327, WO-A 00/48157, WO-A 00/26739, WO-A 94/20940, U.S. Pat. No. 6,799,476, U.S. Pat. No. 6,577,989, U.S. Pat. No. 6,662,120, U.S. Pat. No. 6,574,515, U.S. Pat. No. 6,535,161, U.S. Pat. No. 6,512,358, U.S. Pat. No. 6,480,131, U.S. Pat. No. 6,311,136, U.S. Pat. No. 6,285,094, U.S. Pat. No. 6,269,701, U.S. Pat. No. 6,140,940, U.S. Pat. No. 6,014,100, U.S. Pat. No. 5,959,372, U.S. Pat. No. 5,742,225, U.S. Pat. No. 5,672,975, U.S. Pat. No. 5,535,243, U.S. Pat. No. 5,416,723, U.S. Pat. No. 5,207,101, U.S. Pat. No. 5,068,592, U.S. Pat. No. 4,926,340, U.S. Pat. No. 4,656,353, U.S. Pat. No. 4,317,116, U.S. Pat. No. 3,764,880, US-A 2008/0015799, U.S. Pat. No. 7,200,503, U.S. Pat. No. 7,630,844, WO-A 00/67087, WO-A 2010/014102, EP-A 1 147 841, EP-A 1 058 093, EP-A 525 920 or DE-A 39 34 007. In given cases, as is, for example, described in U.S. Pat. No. 3,764,880, US-A 2008/0015799, U.S. Pat. No. 7,630,844 or WO-A 2004/048905, a galvanic isolation is provided inside of the transmitter electronics, for example, between the internal driver circuit and the series current controller, in order to prevent that possible, not always safely preventable, potential differences between the plant in which the field device is applied and the external electrical energy supply be uncontrolledly removed. Traditionally, such two-conductor field devices are predominantly designed in such a manner, that an instantaneous electrical current level—set to a level between 4 mA and 20 mA (=milliampere)—of the supply current instantaneously flowing in the single pair line serving as part of a current loop also simultaneously represents the measured value instantaneously produced by the measuring system. Consequently, a particular problem of such two-conductor field devices also lies in the fact that the electrical power at least nominally convertible by or to be converted by the transmitter electronics—in the following, "available power" for short—can, during the operation, fluctuate over a broad range in a practically unpredictable manner. Taking this into consideration, in such measuring systems embodied as two-conductor field devices—and consequently such with (4 mA to 20 mA)-current loops—suitable measures are to be taken, in order optimally (consequently with as low a loss as possible) matched to the instantaneous measuring and operational situation, to distribute the available power—which at times even amounts to considerably less than 100 mW—to the individual components, or to electronic assemblies of the measuring system, consequently to the driver circuit and the measuring and operating circuit. In the case of measuring systems designed as two-conductor field device with active measuring transducers, the total electrical power instantaneously converted in the measuring system, such as is discussed, among others, in U.S. Pat. No. 6,799,476, U.S. Pat. No. 6,014,100, US-A 2008/0015799, U.S. Pat. No. 7,200,503, U.S. Pat. No. 7,630,844, WO-A 2010/014102 or WO-A 02/103327, can, for example, optimally be utilized in the measuring system, so that the electrical power converted in the measuring transducer is matched—ad hoc or predictively—to the instantaneously available power, for example, via a correspondingly adapted clocking of the driver signal and/or via lessening a maximal electrical current level and/or a maximal voltage level of the driver signal.

For optimal distribution of the available electrical power in the measuring system, in, for example, US-A 2008/0015799, U.S. Pat. No. 7,200,503, U.S. Pat. No. 7,630,844, the application of two voltage controllers is provided, of which a first voltage controller delivers to a controller output a variable direct voltage for operating the driver circuit, and a second voltage controller delivers to a controller output a direct voltage—which is independent from the aforementioned operating voltage of the driver circuit, and consequently essentially constantly controlled to a predeterminable voltage level—for operating the measuring and operating circuit. By means of the direct voltage or a secondary voltage branching therefrom, an end stage is operated, which converts a control signal, which is present at a signal input, and which is especially bipolar and/or at least at times periodic, into the driver signal for the measuring transducer or its actuator, and consequently acts as a power amplifier for the control signal, wherein, not least of all for the previously mentioned measuring transducer of vibration type, the driver signal is usually to be set as precisely as possible as regards its electrical current level.

Especially for the above-described case, in which, during operation of a measuring system of the type being discussed, the available electrical power is, as a result of a small magnitude of the measured variable to be registered, equally small—for instance, less than 100 mW—the required electrical current level occasionally can no longer be set by means of the end stage, and, in this respect, the driver signal can no longer be delivered with the required signal quality, or a converting of the control signal into a driver signal having said electrical current level could, as a result of back couplings in the assemblage of the voltage controller, lead to an overloading or a destabilizing of the entire internal voltage supply, along with an at times increased power or energy requirement solely for the return of the measuring system, and consequently of the driver circuit and of the measuring transducer, back to a stable working point or operating state.

SUMMARY OF THE INVENTION

Proceeding therefrom, an object of the invention is to provide a driver circuit suitable for measuring systems of the described type—consequently two-conductor field devices with active measuring transducers—wherein such driver circuit enables, as energy efficiently with regard to its electrical current level as possible, an adjustable driver signal to be generated with a sufficiently high signal quality, even in the case of comparatively small available power in the measuring system.

For achieving the object, the invention resides in a driver circuit for an actuator—for example, for an electro-mechanical, electro-acoustic or electro-magnetic exciter of a physical-to-electrical measuring transducer—wherein the driver circuit has a voltage controller, which delivers to a controller output a first direct voltage, for example controlled to a predeterminable desired value and/or always amounting to more than 1.5 V (=volt) and less than 20 V; a direct voltage converter, to which is applied on the primary side the first direct voltage—which is delivered by the voltage controller, and which, for example, at times amounts to less than a predetermined voltage threshold value and/or is variable within a predetermined voltage interval—and which converts this first direct voltage into a second direct voltage, which is accessible on the secondary side, and which, for example, is variable and/or always amounts to less than 3 V; as well as an end stage operated by means of the second direct voltage, this end stage converting a control signal, which is, for example, bipolar and/or at least at times periodic, and present at a signal input—which is, for example, high-resistance and/or has an input resistance of more than 10 kΩ (=kiloohm)—into a driver signal—which is, for example, bipolar and/or at least at times periodic—for the measuring transducer; wherein the second direct voltage has a magnitude which is always smaller than a magnitude of the first direct voltage, and wherein the driver signal has an electrical power which is higher than an electrical power of the control signal.

Additionally, the invention resides in a transmitter electronics having such a driver circuit, and having a measuring and operating circuit for at least one measurement signal delivered by a physical-to-electrical measuring transducer—for example, a measuring transducer of vibration type or an HF transmitting/receiving transducer—having an (for example inductive) actuator, for example, an electro-mechanical, electro-acoustic or electro-magnetic exciter.

Moreover, the invention resides in a measuring system having such a—for example, also intrinsically safe—transmitter electronics, and having a physical-to-electrical measuring transducer electrically connected both with its driver circuit as well as its measuring and operating circuit, for example, a measuring transducer of vibration type having at least one vibrating measuring tube for producing at least one measurement signal dependent on or corresponding with a—for example, variable and/or fluctuating—physical measured variable, for example, mass flow rate and/or density and/or viscosity of a fluid conveyed in a pipeline or fill level of a bulk goods medium held in a container.

According to a first embodiment of the driver circuit of the invention, it is provided that the voltage controller provides at its output a fluctuating electrical power, for example in such a manner, that a demand for electrical power by the direct voltage converter is, at times, higher than an electrical power instantaneously available at the output of the voltage controller; and/or that it delivers the direct voltage with a magnitude at times lying below a predetermined voltage threshold value.

According to a second embodiment of the driver circuit the invention, it is provided that the driver circuit furthermore includes an overload detector for registering an overload situation of the voltage controller, for example, by comparing the first direct voltage delivered at the output by the voltage controller with a voltage threshold value predetermined therefor, and/or by comparing the electrical power output at the output of the voltage controller with a power threshold value predetermined therefor, and for producing a load signal, which, for example, also operates the direct voltage converter and/or is binary, and which signals with a first signal level, that the voltage controller is overloaded and/or that a demand of the direct voltage converter for electrical power is instantaneously higher than an electrical power instantaneously available at the output of the voltage controller, or which signals with a second signal level different from the first signal level, that the voltage controller is not overloaded and/or that the electrical power instantaneously available at the output of the voltage controller is sufficient for covering the demand of the direct voltage converter for electrical power. Developing this embodiment of the invention further, it is additionally provided that the direct voltage converter has a control input for turning the direct voltage converter on and off, wherein the load signal produced by the overload detector is fed to the control input. Additionally, the direct voltage converter is arranged in such a way, that, when the load signal has assumed the first signal level, the direct voltage converter is switched off, for example in such a manner, that the direct voltage converter delivers the second direct voltage with a magnitude of less than 1 V and/or that an effective electrical input current driven by the first direct voltage of less than 100 µA (=microampere) can flow, and that, when the load signal has assumed the second signal level, the direct voltage converter is turned on, for example in such a manner, that the direct voltage converter delivers the second direct voltage with a magnitude of more than 1 V and/or that an effective electrical input current driven by the first direct voltage of more than 0.5 mA can flow. Alternatively thereto or in supplementation thereof, it is additionally provided, that the load signal is embodied at least at times as an aperiodic clock signal with variable pulse length and/or with variable pause length and/or with variable pulse-to-pause-ratio, for example in such a manner, that an instantaneous pulse length and/or an instantaneous pause length and/or an instantaneous pulse-to-pause length-ratio of the load signal is dependent on the electrical power instantaneously available at the output of the voltage controller.

According to a third embodiment of the driver circuit the invention, it is provided that the direct voltage converter is embodied as a switching controller, which, for example, is operated only in a pulse frequency modulation mode.

According to a fourth embodiment of the driver circuit of the invention, it is provided that the direct voltage converter is embodied as a buck converter, which, for example, is clocked with a rectangular signal modulated in the duration of its period.

According to a fifth embodiment of the driver circuit of the invention, it is provided that the driver circuit furthermore includes for producing the control signal a digital-to-analog converter, which is operated, for example, by means of the second direct voltage. Developing this embodiment of the invention further, it is additionally provided that, by means of the second direct voltage, a reference voltage of the digital-to-analog converter proportional to such second direct voltage is formed.

According to a first embodiment of the transmitter electronics of the invention, it is provided that the measuring and operating circuit includes a signal generator, which produces a digital signal serving for producing the control signal.

According to a second embodiment of the transmitter electronics of the invention, it is provided that the transmitter electronics furthermore includes a two-conductor connection circuit for connecting the transmitter electronics to a measuring and supply unit remote therefrom. Developing this embodiment of the invention further, the two-conductor connection circuit is additionally arranged so as to obtain electrical power required for operation of the driver circuit from the measuring and supply unit, for example via a (4 mA to mA) current loop, and/or to transmit measured data generated by means of the measuring and operating circuit to the measuring and supply unit, for example, via modulation of an electrical current flowing in the two-conductor connection circuit and/or an electrical current serving for providing electrical power for the driver circuit and/or the measuring and operating circuit.

According to a third embodiment of the transmitter electronics of the invention, it is provided that the measuring and operating circuit has a voltage controller, which delivers to a controller output a third direct voltage, which, for example, is controlled to a predetermined desired value and/or amounts to more than 1 V, and that the measuring and operating circuit also has a microcomputer, which is operated, for example, by means of the third direct voltage and/or embodied as a digital signal processor.

According to a first embodiment of the measuring system of the invention, it is provided that a maximum electrical power instantaneously available at the output of the voltage controller of the operating circuit is dependent on an instantaneous magnitude of the measured variable registered by means of the measuring transducer, for example in such a manner, that, in the case of an increasing magnitude of the measured variable, the maximum instantaneously available electrical power rises, and/or that, in the case of a decreasing magnitude of the measured variable, the maximum instantaneously available electrical power decreases.

According to a second embodiment of the measuring system of the invention, it is provided that a maximum electrical power instantaneously available at the output of the voltage controller of the operating circuit is dependent on an instantaneous magnitude of the measured variable registered by means of the measuring transducer, for example in such a manner, that, in the case of a minimum magnitude of said measured variable predetermined for the measuring system, the maximum instantaneously available electrical power is smaller than in the case of a maximal magnitude of said measured variable predetermined for the measuring system.

According to a third embodiment of the measuring system of the invention, it is provided that the driver circuit includes an overload detector for registering an overload situation of the voltage controller—for example, by comparing the first direct voltage delivered at the output by the voltage controller with a voltage threshold value predetermined therefor and/or by comparing the electrical power output at the output of the voltage controller with a power threshold value predetermined therefor—and for producing a load signal, which, for example, is also binary and/or operates the direct voltage converter, and which signals with a first signal level that the voltage controller is overloaded and/or that a demand of the direct voltage converter for electrical power instantaneously is higher than an electrical power instantaneously available at the output of the voltage controller, or which signals with a second signal level different from the first signal level that the voltage controller is not overloaded and/or that the electrical power instantaneously available at the output of the voltage controller is sufficient for meeting the demand of the direct voltage converter for electrical power. It is also provided that an instantaneous pulse length and/or an instantaneous pause length of the load signal and/or an instantaneous pulse-to-pause ratio is dependent on an instantaneous magnitude of the measured variable registered by means of the measuring transducer, for example in such a manner, that in the case of a minimum magnitude of the measured variable predetermined for the measuring system, said pulse length is smaller than in the case of a comparatively larger magnitude of said measured variable, or that, in the case of a minimum magnitude of said measured variable predetermined for the measuring system, the pause length is larger than in the case of a comparatively larger magnitude of said measured variable and/or that in the case of a minimum magnitude of said measured variable predetermined for the measuring system, said pulse-to-pause ratio is smaller than in the case of a comparatively larger magnitude of said measured variable.

According to a fourth embodiment of the measuring system of the invention, it is provided that a magnitude of the direct voltage instantaneously delivered by the voltage controller of the measuring and operating circuit is independent of an instantaneous magnitude of the measured variable registered by means of the measuring transducer; and/or that a maximum electrical power instantaneously available at the output of the voltage controller of the measuring and operating circuit is independent of an instantaneous magnitude of the measured variable registered by means of the measuring transducer.

According to a fifth embodiment of the measuring system of the invention, it is provided that the measuring transducer has at least one measuring tube, which is excited to mechanical oscillations by means of the actuator which is, for example, embodied as an electrodynamic oscillation exciter and/or formed by means of a plunging armature, coil arrangement.

According to a sixth embodiment of the measuring system of the invention, it is provided that the transmitter electronics is connected to a measuring and supply unit remote therefrom. Developing this embodiment of the invention further, it is additionally provided that the transmitter electronics draws electrical power required for operation of the driver circuit from the measuring and supply unit, and/or that the transmitter electronics transmits measured data generated by means of the measuring and operating circuit—for example mass flow measured values in each case representing a mass flow rate of a medium flowing in a pipeline, density-measured values in each case representing a density of a medium, or viscosity measured values in each case representing a viscosity of a medium—to the measuring and supply unit, for example, via modulation of an electrical current flowing in a two-conductor connection circuit provided in the transmitter electronics.

A basic idea of the invention is to derive as efficiently or with as low-loss as possible, from a controlled—and consequently fluctuating for operational reasons in its voltage level—direct voltage, the driver signal required for an actuator of an active measuring transducer (for instance, a measuring transducer of vibration type)—wherein this signal most often is to be held variable in a broad electrical current and voltage range—via application of a direct voltage converter, embodied as a step-down converter, which converts electrical power across a broad voltage and electrical current range with a very high efficiency; and indeed to do so to the greatest degree possible without appreciable repercussions on the supply circuits delivering the direct voltage, and with a high and as constant as possible signal quality across the total working range of the measuring system.

The invention, as well as further advantageous embodiments, will now be explained in greater detail on the basis of the appended drawing, the figures of which show examples of embodiments. Equal parts are provided in all figures with the same reference characters; when required for reasons of perspicuity, or when it otherwise appears sensible, already mentioned reference characters are omitted in subsequent figures. Other advantageous embodiments or further developments, especially combinations of aspects of the invention at first explained only individually, will become further evident from the figures of the drawing, as well as from the dependent claims as such.

DETAILED DISCUSSION IN CONJUNCTION WITH THE DRAWINGS

Figure 1:
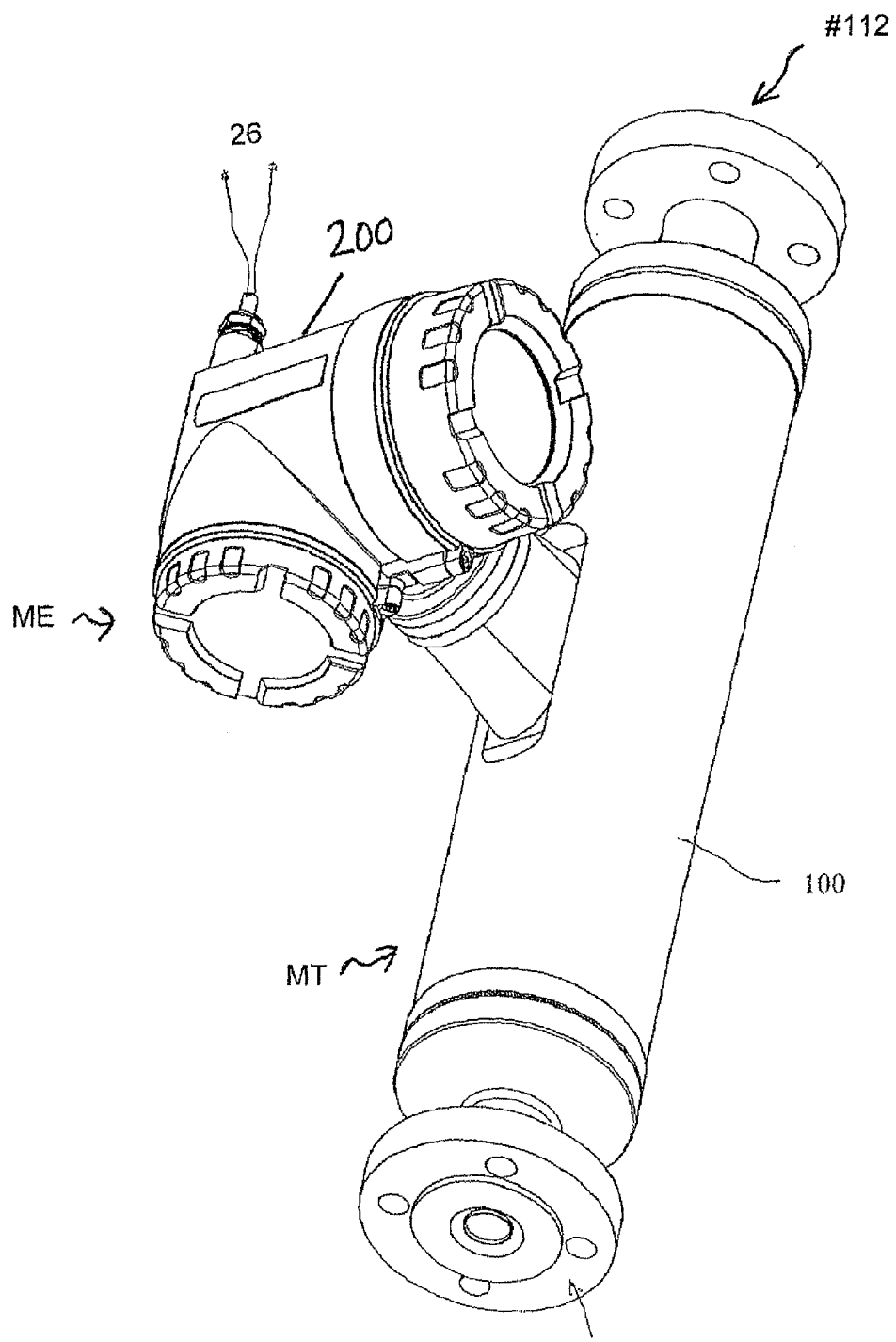
FIG. 1 a measuring system, here embodied as a compact measuring device, for media flowing in pipelines.

FIG. 1 shows a measuring system for flowable, especially fluid, media, which is insertable in a process line—for instance, a pipeline of an industrial plant—and which is formed, for example, by means of a Coriolis mass flow measuring device, density measuring device, viscosity measuring device or the like, the measuring system in the example of an embodiment shown here serving for measuring and/or monitoring at least one additional physical, measured variable of a medium conveyed in the pipeline, such as, for instance, a mass flow rate, a density, a viscosity or the like. The measuring system—here implemented by means of an in-line measuring device of compact construction—includes therefor, connected to the process line via an inlet end #111 as well as an outlet end #112, a physical to electrical measuring transducer MT, which is connected to a transmitter electronics ME of the measuring system, externally supplied during operation with electrical energy especially via a connecting cable and/or by means of internal energy storer. The electrical connecting of the measuring transducer to the aforementioned transmitter electronics can occur by means of corresponding connecting lines, which extend out from the electronics housing 200, for example, via a cable feed-through. The connecting lines can, in such case, be embodied at least partially as electrical line wires at least sectionally encased in an electrical insulation, e.g. in the form of "twisted-pair" lines, flat ribbon cables and/or coaxial cables. Alternatively thereto or in supplementation thereof, the connecting lines can also at least sectionally be formed by means of the conductive traces of a circuit board, especially a flexible, and, in given cases, lacquered circuit board.

The measuring transducer MT involves an active measuring transducer, which, by means of an actuator 5—for example, an electro-mechanical, electro-acoustic or electro-magnetic exciter—correspondingly converts a driver signal $i_{exc}$—which is electrical and, for example, bipolar and/or at least at times periodic, and which is here delivered by the transmitter electronics ME—and consequently its electrical signal power $P_{exc}$, into a measurable effect useful for registering the measured variable, such as, for instance, Coriolis forces or induced voltages in the medium. The measuring transducer MT can accordingly be, for example, a flow-measuring transducer correspondingly flowed through during operation by the medium to be measured (such as, for instance, a liquid and/or a gas), not least of all also a measuring transducer of vibration type with at least one vibrating measuring tube and an electro-mechanical oscillation exciter acting thereon, a magneto-inductive measuring transducer for conductive liquids, or an ultrasound-measuring transducer for fluids, having at least one acoustic transmitter, or, for example, also an HF transmitting/receiving transducer for electromagnetic microwaves working according to the echo principle. For the mentioned case, in which the measuring transducer MT is one of vibration type for flowing media, according to an additional embodiment of the invention, it is provided that the measuring transducer has at least one measuring tube, which, by means of the actuator—which is, for example, embodied as an electrodynamic oscillation exciter and/or formed by means of a plunging armature, coil arrangement, and therefore consequently inductive—is excited to execute mechanical oscillations, and consequently to such oscillations, which, as a result of Coriolis forces in the medium flowing through the measuring transducer, have an oscillation form dependent on an instantaneous mass flow rate and/or a resonance frequency dependent on an instantaneous density of the medium conveyed into the measuring transducer and/or an attenuation dependent on an instantaneous viscosity of the medium conveyed in the measuring transducer.

Figure 2:
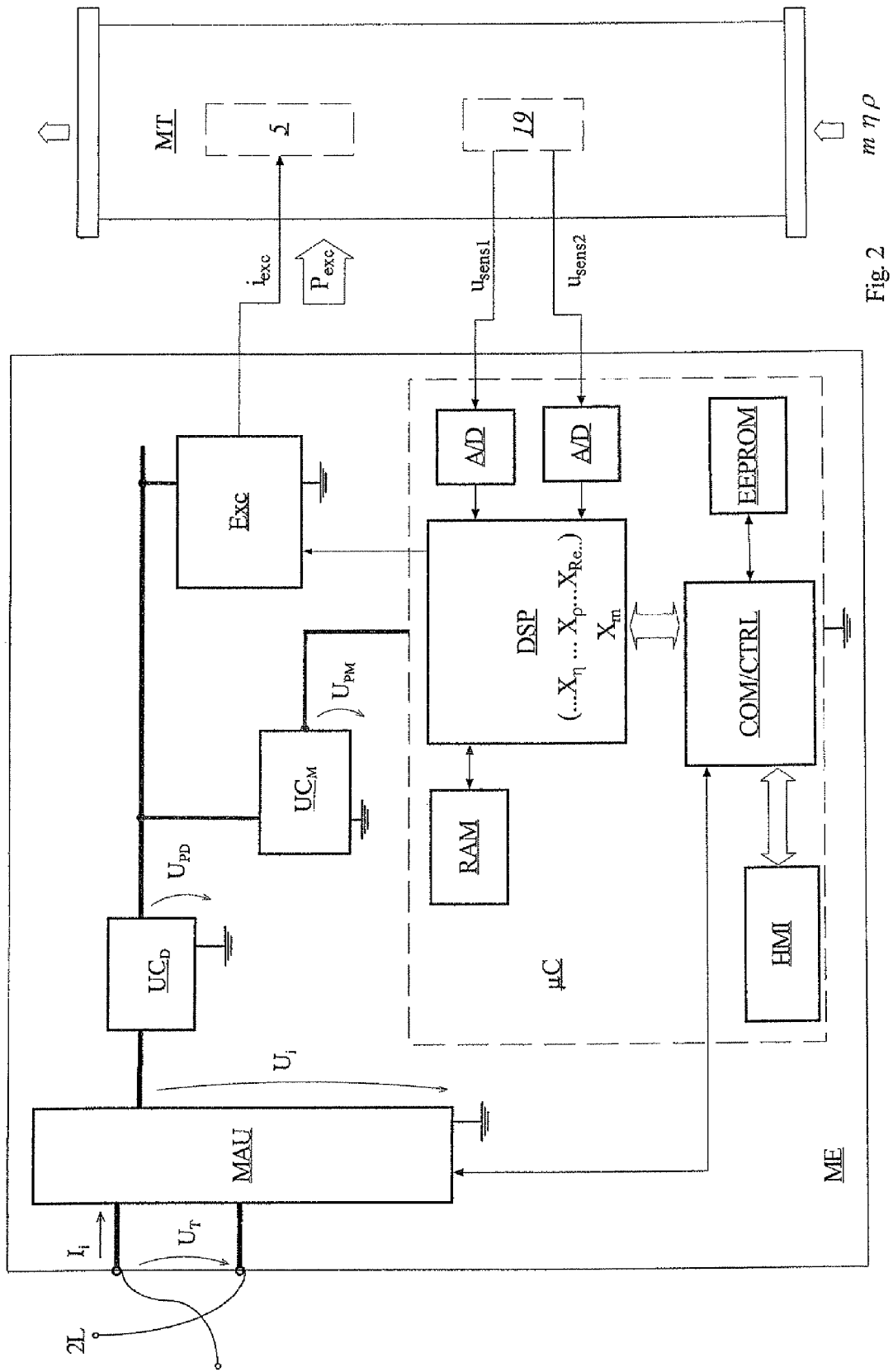
FIG. 2 schematically, in the manner of a block diagram, a transmitter electronics, especially a transmitter electronics suitable for a measuring system according to FIG. 1, with an active measuring transducer connected thereto.

The transmitter electronics ME, which, for example, is also intrinsically safe and/or nominally operated with a maximal power of 1 W or less, includes—as is schematically represented in FIG. 2 in the manner of a block diagram: A driver circuit Exc, which serves for activating the measuring transducer and not least of all also generates the aforementioned driver signal; and a measuring- and operating circuit μC, which 1) processes measurement signals $u_{sens1}$, $u_{sens2}$, delivered from the measuring transducer MT or, as the case may be, more particularly, from a sensor arrangement 19 provided in the measuring- and operating circuit μC and formed, for instance, by means of electrodynamic oscillation sensors, 2) is formed, for example, by means of a digital signal processor DSP and/or 3) communicates with the driver-circuit Exc during operation. During operation, this measuring and operating circuit μC delivers measured values representing the at least one measured variable, such as, for example, the instantaneous mass flow or a totaled mass flow. The measurement signals generated by the measuring transducer—which, for example, are in each case formed as oscillation measurement signals, and which, in the case of a measuring transducer of vibration type, in each case have a signal component with a signal frequency corresponding to an instantaneous oscillation frequency, $f_{exc}$, of the at least one oscillating measuring tube—are, consequently (as is also shown in FIG. 2,), fed to the transmitter electronics ME, and there, to the measuring and evaluating circuit μC provided therein, where, by means of a corresponding input circuit IC, they are first preprocessed—especially preamplified, filtered and digitized, in order to be able to be suitably evaluated. According to an additional embodiment of the invention, the measuring and operating circuit μC is implemented by means of a microcomputer—for example, one implemented by means of a digital signal processor DSP—provided in the transmitter electronics ME, and, by means of program code correspondingly implemented in and running in this. The program code can, for example, be stored persistently in a non-volatile data memory EEPROM of the microcomputer and, in the case of starting the code, can be loaded in a volatile data memory RAM, e.g. one integrated in the microcomputer. Of course, the measurement signals, as already indicated, are, for a processing in the microcomputer, to be converted by means of corresponding analog-to-digital-transducer A/D of the transmitter electronics ME into corresponding digital signals; compare in this connection, for example, the previously mentioned U.S. Pat. No. 6,311,136.

The driver-circuit Exc and the measuring and operating circuit μC, as well as other electronics components of the transmitter electronics serving the operation of the measuring system, such as, for instance, internal energy supply circuits for providing internal supply direct voltages, a connection circuit MAU serving the connection to a superordinated measurement data processing system or an external fieldbus and/or a control electronics COM/CNTRL of the measuring and operating circuit μC serving the internal operational control of the measuring system, are additionally accommodated in a corresponding electronics housing 200, which is especially embodied in an impact-resistant and/or explosion-resistant and/or hermetically sealed manner. For visualization of measuring-system-internally produced measured values and/or, in given cases, measuring-system-internally generated status reports—such as, for instance, an error report or an alarm—the measuring system can, furthermore, have a display and operating element HMI on-site, which, at least at times, communicates with the transmitter electronics, such as, for instance, an LCD, OLED or TFT display placed in the electronics housing behind a window correspondingly provided therein, as well as a corresponding input keypad and/or a touch screen.

In advantageous manner, the transmitter electronics ME, especially a programmable and/or remotely parameterable, transmitter electronics, can additionally be designed in such a manner, that, during operation of the measuring system, it can, via a data transmission system—for example, a fieldbus system and/or wirelessly by radio—exchange measurement data and/or other operating data—such as, for instance, current measured values or settings and/or diagnostic values serving for control of the measuring system—with a superordinated electronic data processing system, for example, a programmable logic controller control (PLC), a personal computer and/or a work station. In such case, the transmitter electronics ME can, for example, have a connection circuit of such a sort, which during operation is fed by a measuring and supply unit provided in the data processing system, remote from the measuring system. The transmitter electronics can, in such case, furthermore especially be embodied in such a manner, that it is, by means of a two-conductor connection 2L—configured, for example, as 4-20 mA-current loop—electrically connectable with the external electronic data processing system, and consequently with the aforementioned measuring and supply unit, and, via this, is supplied with electrical energy and can transmit measured values to the data processing system.

In an embodiment of the invention, the transmitter electronics consequently additionally includes a two-conductor connection circuit MAU for connecting the transmitter electronics to a measuring and supply unit remote therefrom. Additionally, it is in such case provided that the transmitter electronics draws electrical power required for its operation, and consequently for the operation of the driver circuit, from the measuring and supply unit, for instance, in the form of a supply direct current $I_i$ fed in a via (4 mA to 20 mA) current loop by the measuring and supply unit, and a terminal voltage $U_T$ corresponding therewith, at an input of the two-conductor connection circuit MAU. Moreover, the transmitter electronics, and consequently the two-conductor connection circuit MAU, is arranged so as to transmit measured data generated by means of the measuring and operating circuit—for instance, mass flow-measured values representing mass flow rate of a medium flowing in a pipeline, density measured values representing density of a medium, or viscosity measured values representing viscosity of a medium—to the measuring and supply unit, for example, via modulation of an electrical current flowing in a two-conductor connection circuit MAU provided in the transmitter electronics, this electrical current not least of all also serving for supplying the transmitter electronics, and consequently serving for providing electrical power for the driver circuit and/or the measuring and operating circuit. For forming the two-conductor connection circuit MAU—not least of all also in the aforementioned case, in which said two-conductor connection circuit MAU is part of a (4 mA to 20 mA) current loop—conventional series current controllers and/or parallel current controllers, for example, can, not least of all also serve the purpose of providing an internal input voltage $U_i$ largely stable at least within a steady working point of the measuring system.

As already mentioned, the efficiency with which measuring systems of the type being discussed, for instance two-conductor field devices, convert the available electrical power into measured values is not least of all also dependent on the fact that the driver circuit on the one hand works energy efficiently, but that it also, on the other hand, to the greatest extent possible, does not provoke in the internal energy supply in the measuring system any voltage fluctuations disturbing the operation of the measuring circuit. The driver circuit of the invention includes for this the following basic construction schematically shown in FIG. 3 and, derived therefrom, the following manner of operation: A voltage controller $UC_D$ delivers to a controller output a first direct voltage $U_{PD}$, which, for example, is controlled to a predeterminable desired value and/or always amounts to more than 1.5 V (=volt) and less than 10 V. The direct voltage $U_{PD}$, which is delivered by the voltage controller and, for example, at times amounts to less than a (actuator- or measuring transducer-specific) predetermined voltage threshold value and/or is variable within a predetermined voltage interval, is, later in the process, applied on the primary side to a direct voltage converter DC/DC, which converts this voltage into a second direct voltage $U'_{PD}$, which is variable not least of all also because of fluctuations in the total available electrical power in the transmitter electronics and is accessible on the secondary side. The direct voltage converter DC/DC is, in the case of the driver circuit of the invention, designed in such a manner, that the second direct voltage $U'_{PD}$ has a magnitude that is always smaller than a magnitude of the first direct voltage $U_{PD}$, i.e. the direct voltage converter DC/DC is embodied as a so-called step-down converter. For its implementation, a TPS62xxx of the firm Texas Instruments, consequently a TPS62240 or a TPS6205x, can be used, for example.

Additionally, the driver circuit includes an end stage operated by means of the direct voltage $U'_{PD}$ present at the secondary side of the direct voltage converter DC/DC, this end stage serving, for its part, to convert a control signal $\sin_{exc\_A}$—which, for example, is bipolar and/or, at least at times, periodic—present at a signal input—especially a high-resistance signal input and/or one having an input resistance of more than 0.5 MΩ—into the driver signal $i_{exc}$ for the measuring transducer, and consequently to strengthen it in such a manner, that the driver signal $i_{exc}$, which corresponds to the control signal $\sin_{exc\_A}$, or, in given cases, only corresponds to an amplitude modulation thereof, has an electrical power $P_{exc}$, which, as a result, is higher than an electrical power $P_{sin}$ of the control signal $\sin_{exc\_A}$.

As already mentioned, the voltage controller $UC_D$ provides at its output an electrical power, which fluctuates when considered over a certain operational time frame, and consequently also provides this in such a manner, that a demand of the direct voltage converter DC/DC for electrical power is at times higher than an electrical power instantaneously available at the output of the voltage controller, or the voltage controller $UC_D$ delivers the direct voltage with a magnitude at times lying below a predetermined voltage threshold value. As a result, an overload situation thus at times arises at the voltage controller—for instance, as a result of a very small power instantaneously available in the measuring system—in which case the driver circuit is undersupplied with respect to the electrical power actually to be instantaneously provided by means of the driver signal $i_{exc}$ to the actuator of the measuring transducer. In measuring systems of the type being discussed, such overload situations can, for example, occur when, on the one hand, the measured variable to be registered—thus, for example, the mass flow rate or the density—has a low magnitude, and, on the other hand, the driver signal is simultaneously needed at a higher electrical power—in the case of a measuring transducer of vibration type, for instance, as a result of a comparatively high damping of the oscillations of the at least one measuring tube.

For registering such an overload situation of the voltage controller, not least of all also for the purpose of signaling said overload situation and/or for the load-dependent controlling of the direct voltage converter DC/DC, according to an additional embodiment of the invention, the driver circuit additionally includes a overload detector, for example, one formed by means of a comparator of the first direct voltage $U_{PD}$ delivered at the output of the voltage controller with a voltage threshold value predetermined therefor. The overload detector is especially designed to produce—for example, by comparing the first direct voltage $U_{PD}$ delivered by the voltage controller at the output with the voltage threshold value predetermined therefor, or also by comparing the electrical power output at the output of the voltage controller with a power threshold value predetermined therefor—a (for example binary) load signal en, which signals with a first signal level (L), that the voltage controller is overloaded, or that a demand of the direct voltage converter DC/DC for electrical power instantaneously is higher than an electrical power instantaneously available at the output of the voltage controller, or which signals with a second signal level (H) different from the first signal level that the voltage controller is not overloaded, or that the electrical power instantaneously available at the output of the voltage controller is sufficient for meeting the demand of the direct voltage converter DC/DC for electrical power. As a result of this, the load signal is at least at times—here for the duration of such an occasionally arising overload situation—embodied as an aperiodic clock signal with a variable pulse length and/or with variable pause length and/or with variable pulse-to-pause ratio. In such case, an instantaneous pulse length—and consequently also a pause length or a pulse-to-pause ratio—of the load signal is dependent on the electrical power instantaneously available at the output of the voltage controller, and namely in such a manner, that, in the case of a minimum electrical power predetermined for the driver circuit, said pulse length is smaller than in the case of a comparatively larger electrical power, or that, in the case of increasing electrical power, said pulse length is larger, or in such a manner, that, in the case of a minimum electrical power predetermined for the driver circuit, said pause length is larger than in the case of a comparatively larger electrical power, or that, in the case of increasing electrical power, said pause length is smaller. Associated therewith, in the case of a minimum electrical power predetermined for the driver circuit, said pulse-to-pause length ratio is also smaller than in the case of a comparatively larger electrical power, or said pulse-to-pause length ratio is larger in the case of increasing electrical power.

Figure 3:
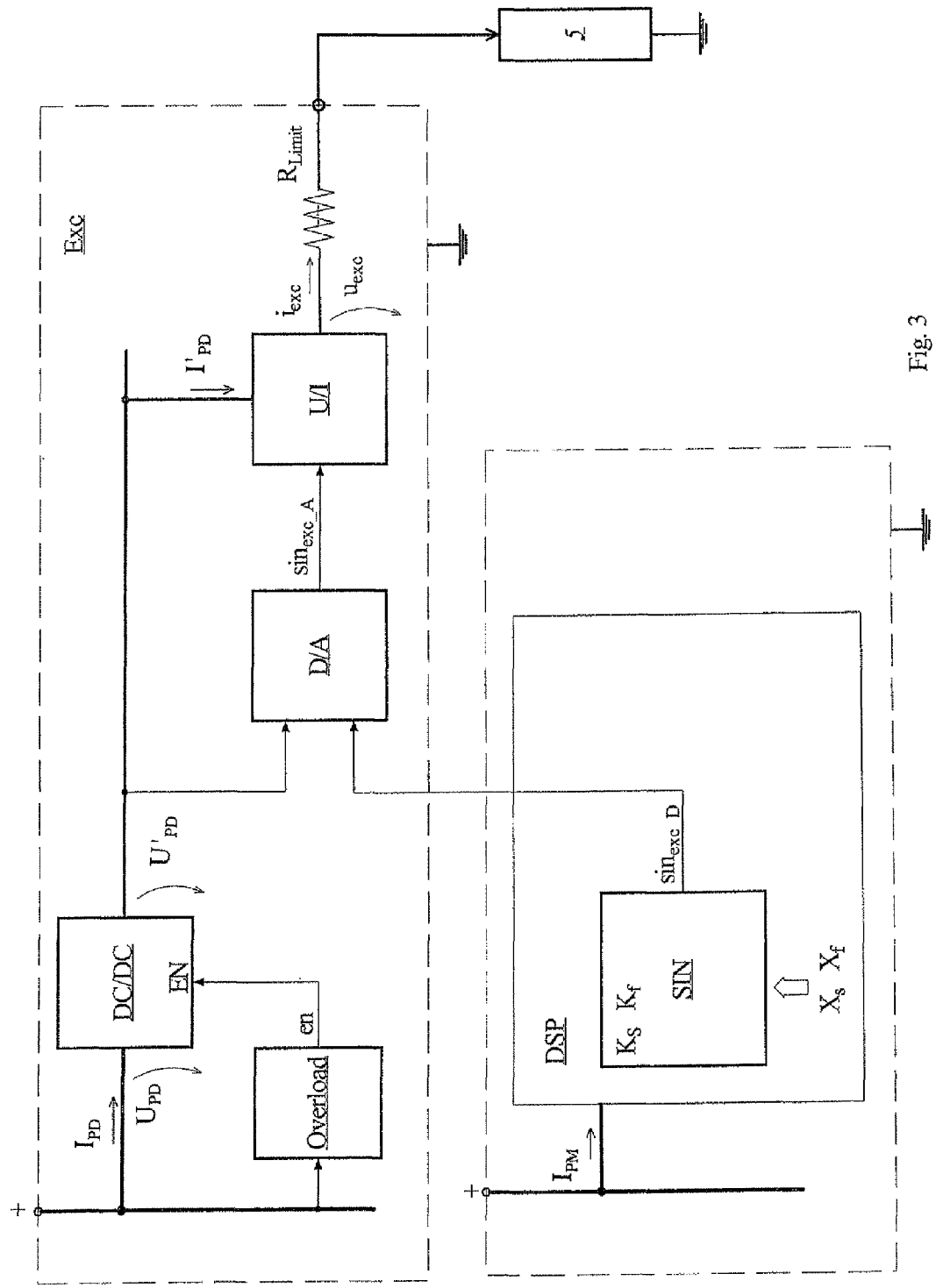
FIG. 3 schematically, in the manner of a block diagram, a driver circuit, especially a driver circuit suitable for a transmitter electronics according to FIG. 2 and consequently for a measuring system according to FIG. 1, for an active measuring transducer, and consequently for a measuring transducer of vibration type with at least one oscillating measuring tube.

According to an additional embodiment of the invention, the direct voltage converter DC/DC includes a control input EN for turning the direct voltage converter DC/DC on and off. Said control input EN, as is schematically presented in FIG. 3, is fed the load signal en produced by the overload detector. The direct voltage converter DC/DC is additionally adapted, matched to the load signal en, in such a manner, that, when the load signal has assumed the first signal level (L), the direct voltage converter DC/DC is switched off, and that the direct voltage converter DC/DC is turned on when the load signal has assumed the second signal level (H). Additionally, according to an additional embodiment of the invention, the direct voltage converter DC/DC is adapted in such a manner, that, in the turned-off state, it delivers the second direct voltage $U'_{PD}$ with a magnitude of in any event less than 1 V, or allows to flow an effective input electrical current $I_{PD}$— driven by the first direct voltage $U_{PD}$, and here thus a residual electrical current of the direct voltage converter DC/DC—of less than 100 µA, and in such a manner, that, in the turned-on state, it delivers the second direct voltage $U'_{PD}$ with a magnitude of more than 1 V, or allows to flow an effective input electrical current $I_{PD}$ driven by the first direct voltage $U_{PD}$ of more than 0.5 mA. According to an additional embodiment of the invention, the direct voltage converter DC/DC is—not least of all also for the purpose of achieving as high a degree of efficiency as possible for the driver circuit as a whole—embodied as a switching controller—for example, one operated only in a pulse frequency modulation mode—and/or as a buck converter, for example, one clocked for the purpose of reducing the aforementioned residual electrical current with a rectangular signal (PFM) modulated in the duration of its period. For the aforementioned case, in which the direct voltage converter DC/DC is formed by means of a TPS62xxx, the latter can accordingly be operated, for example, in the so-called "power save mode".

According to an additional embodiment of the invention, it is additionally provided that the control signal $\sin_{exc\_A}$ is derived from an earlier digital signal $\sin_{exc\_D}$, formed, for instance, by means of the measuring and operating circuit µC. For such purpose, according to an additional embodiment of the invention, the driver circuit includes a corresponding digital-to-analog converter D/A for producing the control signal $\sin_{exc\_A}$. For preventing a possible overdriving of the end stage, it is additionally provided that the second direct voltage $U'_{PD}$ be used as the operating voltage of the digital-to-analog converter D/A, but at least to form by means of said direct voltage $U'_{PD}$ a reference voltage of the digital-to-analog converter D/A proportional to the direct voltage $U'_{PD}$, whereby it can easily be assured that, also in the case an overload situation, the control signal $\sin_{exc\_A}$ has a signal amplitude suitably matched to the instantaneous operating voltage of the end stage, and consequently also to its instantaneous control range. For the purpose of producing the digital signal $\sin_{exc\_D}$, a corresponding signal generator—for example, one also implemented by means of the aforementioned digital signal processor—can be arranged in the measuring and operating circuit, for example in such a manner, that said signal generator outputs at a signal output correspondingly connected with a digital input of the digital-to-analog converter D/A the digital signal $\sin_{exc\_D}$ with an amplitude value dependent on a digital actuating value at a corresponding amplitude setting input.

As shown schematically in FIG. 2, the measuring and operating circuit includes a voltage controller $UC_M$, which, at a controller output, delivers a third direct voltage $U_{PM}$, which, for example, is controlled to a predetermined desired value and/or amounts to more than 1 V. The voltage controller $UC_M$ of the measuring and operating circuit and the voltage controller $UC_D$ of the driver circuit can, in such case, additionally be advantageously matched to one another in such a manner, that a maximum electrical power instantaneously available at the output of the voltage controller $UC_D$ of the driver circuit is dependent on an instantaneous magnitude of the measured variable registered by means of the measuring transducer MT—for instance, in such a manner, that, in the case of an increasing magnitude of the measured variable, said electrical power rises, and/or that in the case of a decreasing magnitude of the measured variable, said power decreases—while a maximum electrical power instantaneously available at the output of the voltage controller $UC_M$ of the measuring and operating circuit, and consequently also a magnitude of the direct voltage $U_{PM}$ instantaneously delivered by the voltage controller $UC_M$ of the measuring and operating circuit is independent of an instantaneous magnitude of the measured variable registered by means of the measuring transducer. As indicated in FIG. 2, the direct voltage $U_{PM}$ instantaneously delivered by the voltage controller of the measuring and operating circuit can, for example—not least of all also because of its comparatively high stability—serve as the operating voltage for the aforementioned internal control electronics COM/CNTRL and/or the digital signal processor DSP.

The invention claimed is:

1. A driver circuit for an actuator, said driver circuit comprising:
   a voltage controller which delivers to a controller output a first direct voltage;
   a direct voltage converter, to which is applied, on a primary side, the first direct voltage delivered from said voltage controller, said direct voltage converter converting the first direct voltage into a second direct voltage available on a secondary side; and
   an end stage operated by means of the second direct voltage for converting a control signal lying on a signal input into a driver signal, wherein:
   the second direct voltage exhibits a magnitude which is always smaller than a magnitude of the first direct voltage; and
   the driver signal exhibits an electrical power which is higher than an electrical power ($P_{sin}$) of the control signal.

2. The driver circuit as claimed in claim 1, wherein:
   said voltage controller provides at its output a fluctuating electrical power in such a manner, that a demand of said direct voltage converter for electrical power is, at times, higher than an electrical power instantaneously available at the output of said voltage controller; and/or
   said voltage controller delivers the direct voltage with a magnitude at times lying below a predetermined voltage threshold value.

3. The driver circuit as claimed in claim 1, further comprising:
   an overload detector for registering an overload situation of said voltage controller, wherein:
   the load signal signals with a first signal level: that said voltage controller is overloaded, and/or that a demand of said direct voltage converter for electrical power is instantaneously higher than an electrical power instantaneously available at the output of said voltage controller; or
   the load signal signals with a second signal level different from the first signal level:
   that the voltage controller is not overloaded and/or
   that the electrical power instantaneously available at the output of said voltage controller is sufficient for meeting the demand of said direct voltage converter (DC/DC) for electrical power.

4. The driver circuit as claimed in claim 3, wherein:
   said direct voltage converter has a control input for turning said direct voltage converter on and off; and
   the load signal produced by said overload detector is fed to said control input.

5. The driver circuit as claimed in claim 4, wherein:
   said direct voltage converter is adapted such:
   that, when the load signal has assumed the first signal level, said direct voltage converter is switched off; and
   that, when the load signal has assumed the second signal level, said direct voltage converter is turned on.

6. The driver circuit as claimed in claim 4, wherein:
   said direct voltage converter is adapted such: that, when the load signal has assumed the first signal level, said direct voltage converter is switched off in such a manner, that said direct voltage converter delivers the second direct voltage with a magnitude of less than 1 V and/or that an effective electrical input current driven by the first direct voltage amount to less than 100 μA; and
   that, when the load signal has assumed the second signal level, said direct voltage converter is turned on in such a manner, that said direct voltage converter delivers the second direct voltage with a magnitude of more than 1 V and/or that an effective electrical input current driven by the first direct voltage amounts to more than 0.5 mA.

7. The driver circuit as claimed in claim 3, wherein:
   the load signal is embodied at least at times as an aperiodic clock signal with variable pulse length and/or with variable pause length and/or with variable pulse-to-pause ratio.

8. The driver circuit as claimed in claim 3, wherein:
   an instantaneous pulse length of the load signal is dependent on the electrical power instantaneously available at the output of said voltage controller; and/or
   an instantaneous pause length of the load signal is dependent on the electrical power instantaneously available at the output of said voltage controller; and/or
   an instantaneous pulse-to-pause length ratio of the load signal is dependent on the electrical power instantaneously available at the output of said voltage controller.

9. The driver circuit as claimed in claim 7, wherein:
   an instantaneous pulse length of the load signal is dependent on the electrical power instantaneously available at the output of said voltage controller in such a manner, that, in case of a minimum electrical power predetermined for the driver circuit, said pulse length is smaller than in the case of a comparatively larger electrical power, or that, in case of increasing electrical power, said pulse length is larger; and/or wherein:

an instantaneous pause length of the load signal is dependent on the electrical power instantaneously available at the output of said voltage controller in such a manner, that, in the case of a minimum electrical power predetermined for the driver circuit, said pause length is larger than in the case of a comparatively larger electrical power, or that, in the case of increasing electrical power, said pause length is smaller; and/or wherein:

an instantaneous pulse-to-pause length ratio of the load signal is dependent on the electrical power instantaneously available at the output of said voltage controller in such a manner, that, in the case of a minimum electrical power predetermined for the driver circuit, said pulse-to-pause length ratio is also smaller than in the case of a comparatively larger electrical power, or said pulse-to-pause length ratio is larger in the case of increasing electrical power.

10. The driver circuit as claimed in claim 3, wherein the overload detector registers said overload situation of said voltage controller by comparing the first direct voltage delivered at the output of said voltage controller with a voltage threshold value predetermined therefor, and/or by comparing the electrical power delivered at the output of said voltage controller with a power threshold value predetermined therefor; and/or wherein said load signal operates said direct voltage converter; and/or wherein said load signal is binary.

11. The driver circuit as claimed in claim 1, wherein: said direct voltage converter (is embodied as a switching controller.

12. The driver circuit as claimed in claim 11, wherein: said direct voltage converter is operated only in a pulse frequency modulation mode.

13. The driver circuit as claimed in claim 1, wherein: said direct voltage converter is embodied as a buck converter.

14. The driver circuit as claimed in claim 13, wherein: said direct voltage converter is clocked with a rectangular signal modulated in the duration of its period.

15. The driver circuit as claimed in claim 1, further comprising:
a digital-to-analog converter for producing the control signal.

16. The driver circuit as claimed in claim 15, wherein: by means of the second direct voltage, a reference voltage of said digital-to-analog converter proportional to the second direct voltage is formed.

17. Transmitter electronics, comprising:
a driver circuit as claimed in claim 1; and
a measuring and operating circuit for at least one measurement signal delivered from a physical-to-electrical measuring transducer including an actuator.

18. The transmitter electronics as claimed in claim 17, wherein:
said measuring and operating circuit includes a signal generator, which produces a digital signal.

19. The transmitter electronics as claimed in claim 17, further comprising:
a two-conductor connection circuit for connecting the transmitter electronics to a measuring and supply unit remote therefrom.

20. The transmitter electronics as claimed in claim 19, wherein:
said two-conductor connection circuit is adapted to draw electrical power required for operation of said driver circuit from said measuring and supply unit.

21. The transmitter electronics as claimed in claim 19, wherein:
said two-conductor connection circuit is adapted to transmit measured data generated by means of said measuring and operating circuit to said measuring and supply unit.

22. The transmitter electronics as claimed in claim 21, wherein:
said two-conductor connection circuit is adapted to transmit measured data generated by means of said measuring and operating circuit to said measuring and supply unit via modulation of an electrical current flowing in said two-conductor connection circuit; and/or wherein
said two-conductor connection circuit is adapted to transmit measured data generated by means of said measuring and operating circuit to said measuring and supply unit via modulation of an electrical current serving for providing electrical power for said driver circuit and/or said measuring and operating circuit.

23. The transmitter electronics as claimed in claim 19, wherein: said two-conductor connection circuit is adapted to draw electrical power required for operation of said driver circuit from said measuring and supply unit via a (4 mA to 20 mA) current loop.

24. The transmitter electronics as claimed in claim 17, wherein:
said measuring and operating circuit includes:
a voltage controller, which delivers to a controller output a third direct voltage and
a microcomputer operated by means of the third direct voltage.

25. The transmitter electronics as claimed in claim 24, wherein:
the third direct voltage is controlled to a predetermined desired value; and/or wherein:
the third direct voltage amounts to more than 1 V.

26. A measuring system, comprising:
a transmitter electronics as claimed in claim 17; and
a physical-to-electrical measuring transducer electrically connected both with said driver circuit of the transmitter electronics as well as with said measuring and operating circuit of the transmitter electronics.

27. The measuring system as claimed in claim 26, wherein:
a maximum electrical power instantaneously available at the output of said voltage controller of the operating circuit is dependent on an instantaneous magnitude of the measured variable registered by means of said measuring transducer.

28. The measuring system as claimed in claim 26, wherein:
a maximum electrical power instantaneously available at the output of said voltage controller of the operating circuit is dependent on an instantaneous magnitude of said measured variable registered by means of the measuring transducer.

29. The measuring system as claimed in claim 26, wherein:
an instantaneous pulse length of the load signal is dependent on an instantaneous magnitude of the measured variable registered by means of said measuring transducer; and/or an instantaneous pause length of the load signal is dependent on an instantaneous magnitude of the measured variable registered by means of said measuring transducer; and an instantaneous pulse-to-pause ratio is dependent on an instantaneous magnitude of the measured variable registered by means of said measuring transducer.

30. The measuring system as claimed in claim 26, wherein:
a magnitude of the direct voltage instantaneously delivered by said voltage controller of the measuring and operating circuit is independent of an instantaneous magnitude of the measured variable registered by means of said measuring transducer; and/or
a maximum electrical power instantaneously available at the output of said voltage controller of the measuring and operating circuit is independent of an instantaneous magnitude of the measured variable registered by means of said measuring transducer.

31. The measuring system as claimed in claim 26, wherein:
said measuring transducer includes at least one measuring tube excited to execute mechanical oscillations by means of the actuator.

32. The measuring system as claimed in claim 26, wherein:
the transmitter electronics is connected to a measuring and supply unit remote therefrom.

33. The measuring system as claimed in claim 32, wherein:
the transmitter electronics draws electrical power required for operation of said driver circuit from said measuring and supply unit.

34. The measuring system as claimed in claim 33, wherein:
the transmitter electronics transmits measured data generated by means of the measuring and operating circuit to said measuring and supply unit.

35. The measuring system as claimed in claim 26, wherein:
driver signal is a bipolar and/or at least at times periodic driver signal for the measuring transducer.

36. The measuring system as claimed in claim 26, wherein:
an instantaneous pulse length of the load signal is dependent on an instantaneous magnitude of the measured variable registered by means of said measuring transducer in such a manner, that, in case of a minimum magnitude of the measured variable predetermined for the measuring system, said pulse length is smaller than in case of an comparatively larger magnitude of said measured variable.

37. The measuring system as claimed in claim 26, wherein:
a maximum electrical power instantaneously available at the output of said voltage controller of the operating circuit is dependent on an instantaneous magnitude of said measured variable registered by means of the measuring transducer in such a manner, that, in the case of a minimum magnitude of said measured variable predetermined for the measuring system, the maximum instantaneously available electrical power is smaller than in the case of a maximum magnitude of said measured variable predetermined for the measuring system.

38. The measuring system as claimed in claim 26, wherein:
the measuring transducer includes at least one vibrating measuring tube for producing at least one measurement signal dependent on or corresponding to a physical measured variable selected from: mass flow rate and/or density and/or viscosity of a fluid conveyed in a pipeline or a fill level of bulk goods held in a container.

39. The measuring system as claimed in claim 26, wherein:
a maximum electrical power instantaneously available at the output of said voltage controller of the operating circuit is dependent on an instantaneous magnitude of the measured variable registered by means of said measuring transducer in such a manner, that, in case of an increasing magnitude of the measured variable, the maximum instantaneously available electrical power rises, and/or that, in case of a decreasing magnitude of the measured variable, the maximum instantaneously available electrical power decreases.

40. The measuring system as claimed in claim 26, wherein:
a maximum electrical power instantaneously available at the output of said voltage controller of the operating circuit is dependent on an instantaneous magnitude of said measured variable registered by means of the measuring transducer in such a manner, that, in the case of a minimum magnitude of said measured variable predetermined for the measuring system, the maximum instantaneously available electrical power is smaller than in the case of a maximum magnitude of said measured variable predetermined for the measuring system.

41. The measuring system as claimed in claim 26, wherein transmitter electronics is intrinsically safe.

42. A measuring system, comprising:
a transmitter electronics including a two-conductor connection circuit for connecting the transmitter electronics to a measuring and supply unit remote therefrom, a driver circuit, and a measuring and operating circuit; and, electrically connected both with said driver circuit of the transmitter electronics and with said measuring and operating circuit of the transmitter electronics, a physical-to-electrical measuring transducer for producing at least one measurement signal dependent on or corresponding to a physical measured variable of a fluid conveyed in a pipeline;

said physical measured variable being selected from: mass flow rate, density and viscosity and said measuring transducer including at least measuring tube adapted to execute mechanical oscillations and said measuring transducer including an inductive actuator adapted to execute said mechanical oscillations;

said two-conductor connection circuit being adapted to draw electrical power required for operation of said driver circuit from said measuring and supply unit via a (4 mA to 20 mA) current loop;

and said driver circuit including: a voltage controller for delivering to a controller output a first direct voltage, a direct voltage converter for converting the first direct voltage, applied on a primary side, into a second direct voltage available on a secondary side, and an end stage operated by means of the second direct voltage for converting a control signal lying on a signal input into a driver signal for the measuring transducer; wherein:

the second direct voltage exhibits a magnitude, which is always smaller than a magnitude of the first direct voltage, and the driver signal exhibits an electrical power, which is higher than an electrical power of the control signal.

43. The measuring system as claimed in claim 42, wherein:
the actuator is embodied as an electrodynamic oscillation exciter and/or formed by means of a plunging armature, coil arrangement.

44. The measuring system as claimed in claim 42, wherein:
the first direct voltage amounts to more than 1.5 V and less than 20V, and the second direct voltage is variable and amounts to less than 3 V.

45. The driver circuit as claimed in claim 1, wherein the first direct voltage is controlled to a predeterminable desired value; and/or wherein the first direct voltage always amounts to more than 1.5 V and less than 20V; and/or wherein the first direct voltage at times amounts to less than a predetermined voltage threshold value; and/or wherein the first direct voltage is variable within a predetermined voltage interval; and/or wherein the control signal is bipolar and/or at least at times periodic; and/or wherein the second direct voltage is variable; and/or wherein the second direct voltage always amounts to less than 3 V.

46. The driver circuit as claimed in claim 1, wherein the signal input of said end stage is a high impedance signal input; and/or wherein the signal input of said end stage exhibiting an input impedance of more than 10 kΩ.

* * * * *